(12) United States Patent
Lefenfeld et al.

(10) Patent No.: US 8,197,707 B2
(45) Date of Patent: Jun. 12, 2012

(54) LITHIUM-POROUS METAL OXIDE COMPOSITIONS AND LITHIUM REAGENT-POROUS METAL COMPOSITIONS

(75) Inventors: Michael Lefenfeld, New York, NY (US); James L. Dye, East Lansing, MI (US); Partha Nandi, East Lansing, MI (US); James Jackson, Haslett, MI (US)

(73) Assignee: Signa Chemistry LLC, New York, NY (US)

( * ) Notice: Subject to any disclaimer, the term of this patent is extended or adjusted under 35 U.S.C. 154(b) by 451 days.

(21) Appl. No.: 11/852,820

(22) Filed: Sep. 10, 2007

(65) Prior Publication Data

US 2008/0111104 A1 May 15, 2008

Related U.S. Application Data

(60) Provisional application No. 60/824,964, filed on Sep. 8, 2006.

(51) Int. Cl.
*H01M 4/58* (2010.01)
*B05D 5/12* (2006.01)
(52) U.S. Cl. ................ 252/182.1; 427/123
(58) Field of Classification Search ............ 252/182
See application file for complete search history.

(56) References Cited

U.S. PATENT DOCUMENTS

| | | | |
|---|---|---|---|
| 1,939,647 A * | 12/1933 | Arnold et al. ............ 502/180 |
| 2,377,290 A | 6/1945 | Drake et al. | |
| 2,740,820 A | 4/1956 | Wilson et al. | |
| 3,033,800 A | 5/1962 | Elliott, Jr. et al. | |
| 3,274,277 A | 9/1966 | Bloch et al. | |
| 3,322,495 A | 5/1967 | Magee | |
| 3,679,605 A | 7/1972 | Sanford et al. | |
| 4,168,247 A | 9/1979 | Hayden et al. | |
| 4,248,741 A | 2/1981 | Wernli et al. | |
| 4,440,631 A | 4/1984 | Togari et al. | |
| 4,837,194 A | 6/1989 | Hayden | |
| 5,128,291 A | 7/1992 | Wax et al. | |
| 5,149,889 A * | 9/1992 | Deberitz et al. ............ 568/878 |
| 5,916,838 A | 6/1999 | Wulff-Doring et al. | |
| 6,399,528 B1 | 6/2002 | Krell et al. | |
| 7,410,567 B2 * | 8/2008 | Lefenfeld et al. ......... 208/251 R |

FOREIGN PATENT DOCUMENTS

WO 2008031101 A2 3/2008

OTHER PUBLICATIONS

Levy et. al, Angew. Chem. Int. Ed. Engl. 20 (1981), No. 12, 1033.*
Voltz, et.al., J. Phy.Chem., 1957, 61(6), 756-758.*
House, et al., The Journal of Organic Chemistry, 43(11), 2153 (1978).*
International Search Report from corresponding PCT/US07/78048, dated Sep. 30, 2008.
Written Opinion from corresponding PCT/US07/78048, dated Sep. 30, 2008.

* cited by examiner

*Primary Examiner* — Melvin C Mayes
*Assistant Examiner* — Yun Qian
(74) *Attorney, Agent, or Firm* — J.A. Lindeman & Co., PLLC

(57) ABSTRACT

The invention relates to lithium metal/porous metal oxide compositions. These lithium metal compositions are prepared by mixing liquid lithium metal with a porous metal oxide in an inert atmosphere under exothermic conditions sufficient to absorb the liquid lithium metal into the porous metal oxide pores. The lithium metal/porous metal oxide compositions of the invention are preferably loaded with lithium metal up to about 40% by weight, with about 20% to 40% by weight being the most preferred loading. The invention also relates to lithium reagent-porous metal oxide compositions having RLi absorbed into a porous oxide. The preparation and use of these compositions are also described.

16 Claims, 11 Drawing Sheets

LITHIUM-POROUS METAL OXIDE COMPOSITIONS AND LITHIUM REAGENT-POROUS METAL COMPOSITIONS

RELATED CASE INFORMATION

This application claims priority to U.S. Provisional Patent Application No. 60/824,964, filed Sep. 8, 2006, which is hereby incorporated by reference in its entirety.

FIELD OF THE INVENTION

This invention relates to lithium metal-porous oxide compositions made by the interaction of metallic lithium with porous metal oxide powders, such as alumina gel, and their use to prepare organolithium and lithium amide reagents, both in situ and as solid free flowing easily handled and stored materials. These compositions do not require flammable solvents and/or cold conditions for storage, shipment and use, yet the absorbed lithium and lithium reagents retain their reactivity and synthetic utility.

BACKGROUND OF INVENTION

Organolithium and lithium amide compounds are important reagents used routinely in synthetic chemistry transformations. Traditionally, organolithium reagents are made by combining finely divided lithium metal at low temperature with solutions of haloorganics or by metal-halogen exchange reactions. Lithium amides are most commonly prepared by the deprotonation of amines using an organolithium reagent. However, stability, storage, and handling of organolithium compounds remain problems that often make their use difficult for organic synthesis, including their use to make lithium amides.

Organolithium as used herein, and as commonly used in the art, refers to lithium compounds of carbon-centered anions. Organolithium reagents are synthetically useful because they are strong bases, effective nucleophiles, and effective catalysts for radical and anionic polymerizations. Such reagents are, however, very reactive, often spontaneously catching fire in the presence of air. To control these hazards, they are only commercially available as solutions in hydrocarbon or ether solvents. These solvents can moderate the pyrophoric nature of the organolithiums, but are themselves volatile and flammable, adding further hazards associated with the use of organolithium reagents.

Lithium amide, as used herein, refers to lithium salts of primary and secondary amines. Lithium amide reagents are synthetically useful because they are strong bases, freely soluble in common organic solvents, and highly versatile. These reagents are, however, very reactive and difficult to handle. With some exceptions, they are not available commercially and must be synthesized immediately prior to their use by adding a primary or secondary amine to an organolithium reagent, such as butyllithium.

Lithium metal is commonly used to generate an organolithium reagent, which is an organometallic compound with a direct bond between a carbon and a lithium atom. Since the electropositive nature of lithium places most of the charge density of the bond on the carbon atom, a carbanion species is created. This enables organolithium reagents to act as extremely powerful bases and nucleophiles. Typically, organolithium reagents are synthesized commercially by the reaction of a haloorganic with lithium metal, according to R—X+ 2Li→R—Li+LiX (See U.S. Pat. No. 5,523,447 by Weiss et al. and U.S. Patent Application Publication No. 20060049379 by Emmel et al). A side reaction that occurs during this synthesis, especially with alkyl iodides, is the Wurtz reaction, where the R group couples with itself. This side reaction can be nearly eliminated by using cold temperatures or chlorine or bromine as the halogen. Other methods of creating organolithium reagents include, for example: (i) reacting a organic halide with a radical anion lithium salt, (ii) performing a metal-halogen exchange between an organic halogen compound and an organolithium species (e.g., Gilman, H. et. al., *J. Am. Chem. Soc.* 1932; 54, 1957), (iii) an exchange between an organolithium species and another organometallic compound, (iv) the deprotonation of an organic compound with an organolithium reagent, (v) reductive cleavage of the carbon-heteroatom (such as sulfur, oxygen, phosphorus, or silicon) bonds (e.g., Gilman. H., et. al., *Org. Chem.* 1958; 23, 2044), or (vi) lithium-hydrogen exchange from LiOH and toluene to make benzyl lithium in DMSO (U.S. Patent Application Publication No. 20060170118 by Everett et. al.).

Organolithium reagents, specifically butyllithium (BuLi), methyllithium (MeLi), phenyllithium (PhLi), and others, are widely used as chemical building blocks and as strong bases in both the pharmaceutical and the industrial manufacturing industry. Lithium amides find related applications; for example, lithium diisopropylamide (LDA) and lithium hexamethyldisilazide (LiHMDS) are both strong bases that are also capable of performing enantioselective alkylation by virtue of the strong coordinating ability of lithium (Hilpert, H. *Tetrahedron,* 2001, 57, 7675). Carbon-centered organolithiums, such as nBuLi, are considered to be both powerful nucleophiles and strong bases at the same time. (Askin, D.; Wallace, M. A.; Vacca, J. P.; Reamer, R, A.; Volante, R. P.; Shinkai, I. *J. Org. Chem.* 1992, 57, 2771). These characteristics enable their use as initiators for anionic polymerizations (Hungenberg, Klaus-Dieter; Loth, Wolfgang; Knoll, Konrad; Janko, Lutz; Bandermann, Friedhelm. *Method for producing statistical styrene-butadiene copolymers.* PCT Int. Appl. WO 9936451 A1.

Little can be done to modify the reactivity or selectivity of ordinary organolithium and lithium amide reagents, yet modification is a growing need in many chemical industries, especially for pharmaceutical and polymerization processes. Traditional stir-batch modes of synthesis with either of these types of compounds generate significant quantities of solvent waste, which is undesirable for any chemical process. A cleaner process, which would involve either a solvent-free organolithium or lithium amide material or a packed-bed flow reactor setup, would be ideal for large scale industrial synthesis, as it would decrease solvent disposal issues and might eliminate tedious purification or work-up steps. One solution would be the creation of a solid source of organolithium reagents which could be used in flow chemistry and would control the efficiency and effectiveness of the reagent in a process. This notion has spawned efforts to develop crystalline Grignard reagents (Marcus, V., et. al. *Angew Chem, Int. Ed.* 2000, 39, 3435) and other solid carbanion sources (Davies, S. G. et. al. *J. Am. Chem. Soc.* 1977, 4, 135 and Eaborn, C., et. al. *J. Am. Chem. Soc.* 1994, 116, 12071) in recent years. However, the methods of preparation of these crystalline reagents are typically tedious and specialized for specific carbanion systems, limiting their utility in large-scale applications and their applicability as general carbanion sources. Grignard reagents, the broadest class of carbanion donors, furthermore undergo the Schlenk equilibrium between two equivalents of an alkyl or aryl magnesium halide (2 RMgX) and one equivalent each of the dialkyl- or diarylmagnesium compound (RMgR) and the magnesium halide salt ($MgX_2$). This disproportionation reaction multiplies the reactive species present, and is a sometimes problematic complication in their applications as carbanion sources.

Only a few of the known organolithium compounds, such as butyllithium, methyllithium, and phenyllithium, are commercially available. Many organolithiums that are not commercially available must be prepared from metal-halogen exchange reactions (for a general reference, see Wakefield, B. *Organolithium Methods*; Academic Press: London, 1988) that use one organolithium reagent and an organic halide in an exchange reaction. Alternatively, pure lithium metal and an organic halide can be reacted to form an organolithium. These transformations represent equilibrium reactions between organic halides, lithium metal, lithium halides and organolithium compounds. Synthesizing a clean organolithium product is difficult since there is often contamination with unreacted organic halides, which adds hardship to any large scale process development. Lithiation can also be performed by deprotonation reactions or by reductive cleavage of ethers and thioethers (Schlosser, M. *Organometallics in Syntheses*; Wiley and Sons: Chichester, 1994, 47), the Shapiro method (Shapiro, R. H. *Org. React.* 1976, 23, 405), or arene-catalyzed lithiation (Yus, M.; Ramon, D. J.; *J. Chem. Soc., Chem. Commun.* 1991, 398). These methods begin by utilizing organolithium itself, functioning as a base, and therefore they are not atom-economic from a synthetic standpoint. The approach of directly reacting lithium metal with the halogenated form of the target organic group is strongly avoided in most industries because of the high reactivity and pyrophoric nature of finely divided Li metal. Dispersed lithium prepared in a refluxing hydrocarbon also causes hardship in large scale ups (Joshi, D. K.; Sutton, J. W.; Carver, S.; Blanchard, J. P. *Org. Process Res. Dev.;* 2005; 9(6); 997-1002.). Alternatively, mercury-lithium (Schollkopf, U.; Gerhart, F. *Angew. Chem. Int. Ed. Engl.* 1981, 20, 795), tellurium lithium (Shiner, C. S.; Berks, A. H.; Fisher, A. M. *J. Am. Chem. Soc.* 1988, 110, 957, Hiiro, T.; Mogami, T.; Kambe, N.; Fujiwara, S-I.; Sonoda, N. Synth. Commun. 1990, 20, 703) and tin-lithium (Hoffmann, R. W.; Breitfelder, S.; Schlapbach, A. *Helv. Chim. Acta* 1996, 79, 346) mediated transmetallations are also possible, but mercury, tellurium and tin compounds are generally toxic, making these reagents unsuitable for large scale industrial processes.

In a different strategy from the present invention, alkyllithiums (MeLi, EtLi) are stabilized by adsorbing the alkyllithium onto the surface of a nonporous inorganic support, such as $SiO_2$, CaO, or $Al_2O_3$, and then coated with a paraffin wax (Deberitz et al. U.S. Pat. No. 5,149,889). However, in this case, one has to use pre-made alkyllithium reagents. Then, to activate the reactivity, the user must remove the oil, wax, or hydrocarbon, which can add another undesirable separation step. An additional major difference from the current invention is the fact that the alkyllithium is adsorbed onto the surface of the inorganic support, not absorbed into the support. This strategy highlights the chemical industry's need and desire for stabilized and easily useable alkyllithium reagents.

Like organolithium compounds, lithium amides have a limited commercial availability. While they can be prepared with difficulty from lithium and a primary or secondary amine, they are most conveniently prepared by treatment of a primary or secondary amine with an organolithium reagent. Thus, lithium amide use suffers from many of the same limitations as the organolithium reagents from which they are typically derived. The three most common organolithium reagents used for generating lithium amides are methyllithium, butyllithium, and phenyllithium, which produce methane, butane, and benzene respectively during the reaction. All of these byproducts pose drawbacks in a manufacturing environment since they are all volatile, flammable materials. Methane and butane are flammable gases at room temperature and their generation as stoichiometric byproducts in large scale manufacturing is problematic and costly. Benzene is toxic and a known carcinogen.

A need exists, therefore, to have organolithium and lithium amide reagents available in a dry form that may be easily handled, stored, and used without a significant loss of their reactivity. This invention answers that need.

SUMMARY OF INVENTION

In one embodiment, this invention relates to lithium metal/porous metal oxide compositions. These lithium metal compositions are prepared by mixing liquid lithium metal with a porous metal oxide in an inert atmosphere under exothermic conditions sufficient to absorb the liquid lithium metal into the porous metal oxide pores. The lithium metal/porous metal oxide compositions of the invention are preferably loaded with lithium metal up to about 40% by weight, with about 20% to 40% by weight being the most preferred loading.

In another embodiment, this invention also relates to lithium reagent-porous metal oxide compositions having RLi absorbed into a porous oxide. In formula RLi, R is an alkyl group, an alkenyl group, an alkynyl group, an aryl group, an alkaryl group, or an $NR^1R^2$ group; $R^1$ is an alkyl group, an alkenyl group, an alkynyl group, an aryl group, an alkaryl group; and $R^2$ is hydrogen, an alkyl group, an alkenyl group, an alkynyl group, an aryl group, an alkaryl group.

Accordingly this invention also relates to methods for creating new compositions of lithium, organolithium, and lithium amide species formed and stored inside porous metal oxides, like alumina ($Al_2O_3$, alumina gel). Lithium absorbed into porous $Al_2O_3$ can be used to prepare and form organolithium and lithium amide compounds inside the pores, as well as for in situ generation of carbanions for nucleophilic addition and polymerizations. Pre-made organolithium compounds can also be absorbed into the pores of solid inorganic supports, such as silica or alumina gel, enabling their solvent-free storage and delivery for use in synthetic transformations. These new compositions are solid-state free-flowing powders that are suitable for use in both batch and flow reactors.

DETAILED DESCRIPTION OF THE INVENTION

Figure 1A:
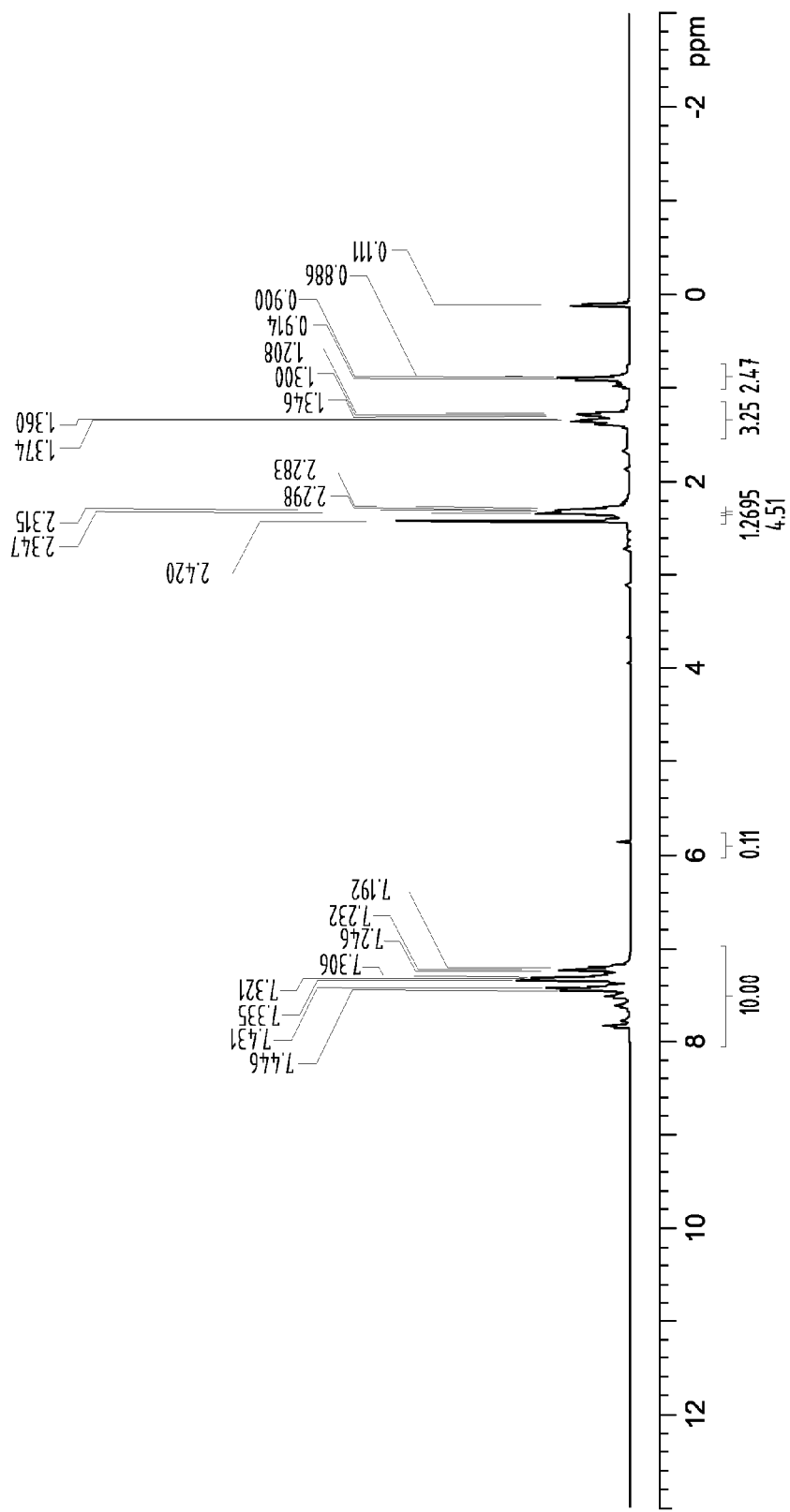
FIGS. 1A-1C shows spectra representative of the results of Example 3.

The ability to utilize alkali metals, their equivalents, and their derivatives in a convenient form continues to be a need in academia, the chemical industry, and for the hydrogen production community. Answering that need, the invention relates to absorbing lithium metal into a porous metal oxide. The porous metal oxides utilized in the composition invention are non-reducible porous metal oxides, porous alumina being a particularly preferred porous metal oxide. The invention also relates to lithium reagent-porous metal oxide compositions, organolithium reagents and lithium amides absorbed into a porous metal oxide. These lithium reagent-porous metal oxide compositions provide a greater variety of accessible nucleophiles and possess significant advantages in handling and storage over currently known lithium reagents.

Lithium Metal-Porous Metal Oxide Compositions

Lithium, the chemical element with the symbol Li, is in Group 1 of the periodic table, among the alkali metals. It is the lightest of all metals and has a density of only half that of water. Lithium is a soft, silvery metal that has a single valence electron, which it readily loses to become a positive ion. Because of this, lithium is flammable and reactive when exposed to oxygen or nitrogen, and especially water. Accordingly, the metal should be stored in a non-reactive atmosphere or in a non-reactive liquid, such as a hydrocarbon or naphtha. Though in Group 1, lithium also exhibits some properties of the alkaline-earth metals in Group 2.

In preparing the lithium-porous metal oxide compositions, lithium metal is preferably mixed with a porous metal oxide (e.g. porous alumina gel) and then heated until the lithium metal melts and is absorbed into the metal oxide pores. One method to accomplish this is heating the lithium metal in an inert atmosphere, such as argon or helium, prior to mixing it with a porous metal oxide. Alternatively, the lithium metal may be mixed as a solid with the porous alumina and the mixture heated to melt the lithium metal. The heat treatment to absorb the lithium metal can range from 160-325° C., preferably between 160-225° C. Another possible way to introduce the lithium metal into the porous alumina is from the vapor phase as done with zeolites (See A. S. Ichimura, J. L. Dye, M. A. Camblor and L. A. Villaescusa, J. Am. Chem. Soc., 124, 1170-1171 (2002) and D. P. Wernette, A. S. Ichimura, S. A. Urbin and J. L. Dye, Chem. Mater. 15, 1441-1448, (2003)). In another possible method, the lithium metal could be deposited into the porous alumina from a metal-ammonia solution (See M. Makesya and K. Grala, Syn. Lett. 1997, pp. 267-268).

A lithium porous metal oxide composition, such as the preferred lithium-alumina gel (Li-AG), may be prepared directly heating a mixture of bulk, or shaved, lithium metal with the calcined porous metal oxide, e.g. alumina, to form loose black powders that retain much of the reducing ability of the parent metals. This reaction preferably occurs in an inert atmosphere, such as in argon or helium. It is believed the lithium-porous metal oxide compositions have small clusters of neutral lithium metal absorbed in the porous metal oxide pores as well as possibly ionized lithium metal (Li⁺) located at the walls of the pores with the electron delocalized from the atom. The materials are pyrophoric, but less reactive in air than finely divided neat lithium metal. The heating of the lithium metal with the porous alumina gel occurs between about 160° C. and about 325° C., preferably between about 160° C. and about 225° C. The heating may be done over a period of time until all of the lithium metal is absorbed, and even overnight.

The lithium metal is believed to be so finely dispersed inside the alumina gel or other porous metal oxides. The lithium-alumina gel is capable of reacting almost completely with nitrogen ($N_2$) gas. The product of the reaction of lithium-alumina gel with nitrogen gas produces finely dispersed lithium nitride ($Li_3N$) inside the pores of the alumina. The reaction of this $Li_3N$ with water calmly produces clean ammonia gas on demand by the following reaction (where AG signifies alumina gel):

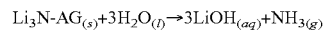

$$Li_3N\text{-}AG_{(s)} + 3H_2O_{(l)} \rightarrow 3LiOH_{(aq)} + NH_{3(g)}$$

This material, therefore, produces ammonia by a method that avoids the hazards of its transportation, transfer, and storage. This pure ammonia can be used for many applications including, but not limited to, the treatment of stack gases containing oxides of nitrogen ($NO_x$) from fossil fuel combustion processes. The lithium-porous metal oxide compositions of the invention may, accordingly, be used to scrub nitrogen gas from inert environments.

The lithium metal-porous metal oxide composition of the invention is preferably loaded with lithium metal up to about 40% by weight, with about 10% to 20% by weight being the most preferred loading.

The porous metal oxides which may be used may be any metal oxide that is not reduced by the lithium metal. The porous metal oxide powder used in this invention that is most preferable is porous alumina (also referred to as alumina gel, particularly γ-alumina gel). Other porous metal oxide powders that may be used for this invention are any transition metal oxide that is not reduced by the lithium metal, such as porous titanium oxide (i.e. TiO, $TiO_2$, $Ti_2O_3$, $Ti_3O_5$), porous calcium oxide (CaO), porous zirconia (i.e. $ZrO_2$), porous iron oxide (i.e. $Fe_2O_3$ or $Fe_3O_4$), porous $CO_3O_4$, porous metal phosphate (MPO), porous hybrid phosphosilicate, porous aluminates, porous alumino silicates, porous vanadates, molybdates, etc. Silica gel can only be used to absorb pre-made solvated organolithium reagents due to the high reactivity between silica and neat lithium metal. Given their porous nature, these porous metal oxides can take up large amounts of absorbed material. The composition of this invention has the lithium metal absorbed inside the pores of the oxide along with the created carbanion or amide species. Porous alumina can be purchased from many companies, such as W.R. Grace & Co. or Almatis AC.

The porous metal oxides used in the porous metal oxide compositions of the invention preferably have average pore sizes ranging from 30 Å to 500 Å. More preferably, the average pore size may range from 60 Å to 190 Å.

Although porous metal oxides, when purchased, are free-flowing powders, they typically contain gaseous material, such as water and air. These are preferably removed prior to mixing the porous oxide powders with lithium metal to form compositions of the invention. The porous metal oxide may be de-gassed using methods known in the art. For example, to remove the gaseous material the porous metal oxide may be heated under vacuum in an evacuable flask, first with a hot air dryer and then with a torch. Such heating achieves temperatures of approximately 300° C. It is also possible, and is actually preferred, to remove the gases more easily and to passivate active sites by heating the porous metal oxide to 600° C. or hotter (~900° C.) in air (calcination). The porous metal oxide is typically cooled to room temperature in a dry (and preferably inert) atmosphere before preparing a composition of the invention.

Lithium Reagent-Porous Metal Oxide Compositions

This invention also relates to lithium reagent-porous metal oxide compositions having RLi absorbed into a porous metal or non-metal oxide. In formula RLi, R is an alkyl group, an alkenyl group, an alkynyl group, an aryl group, an alkaryl group, or an $NR^1R^2$ group; $R^1$ is an alkyl group, an alkenyl group, an alkynyl group, an aryl group, an alkaryl group, an $XR_n$, group (where X can be a heteroatom such as, for example, Si, S, Sn, Ge, P, and n is an integer), or a $Si(R^3)_3$ group; $R^2$ is hydrogen, an alkyl group, an alkenyl group, an alkynyl group, an aryl group, an alkaryl group, or an $Si(R^3)_3$ group; and $R^3$ is an alkyl group, an alkenyl group, an alkynyl group, an aryl group, an alkaryl group. The lithium reagent-porous metal oxide compositions may be prepared by reacting a lithium metal-porous metal oxide composition with an organo halide, RX; by the in situ combination of lithium metal, a porous metal oxide, and an organo halide, RX; by absorption of a lithium reagent, RLi, into a porous metal oxide; or by reacting a lithium metal-porous metal oxide composition with a primary or secondary amine, $HNR^1R^2$. The groups R, $R^1$, $R^2$ and $R^3$ may be further substituted with functional groups or contain heteroatoms such as N, O, S, etc. which do not react with the lithium in such a way as to prevent the formation of a lithium reagent-porous metal oxide composition of the invention. Preferred and exemplary embodiments for R, $R^1$, $R^2$ and $R^3$ are described below.

To prepare a lithium reagent—porous metal oxide composition of the invention, the Li-porous metal oxide composition, prepared as described above, may be cooled in a reaction vessel between about 0° C. and about −78° C. Then a haloorganic compound, or when R=$R^1R^2N$, a primary or secondary amine, (both within RX), is slowly added to the Li-porous metal oxide, either neat or in a solvent. The haloorganic or amine moves into the pores, and reacts with the lithium metal to create the organolithium compound inside the pores of the metal oxide. After the reaction is heated to room temperature, any excess haloorganic, amine, and/or solvent is distilled off to complete the formation of a dry, free-flowing powder of a Li reagent-porous metal oxide composition. As shown in Example 8 below organolithium-porous metal oxide compositions may also be prepared by the reductive cleavage of carbon-heteroatom bond such as vinyllithium from ethyl vinyl ether.

When the lithium reagent is an organo-lithium compound, the haloorganic compounds, RX, that may be used include, but are not limited to, alkyl halides, alkenyl halides aryl halides, and alkaryl halides. Preferred halogens are chloride, bromide, and iodide. The alkyl, alkenyl, and alkynyl groups may be straight or branched chains as well as cyclic and heterocyclic alkyl, alkenyl or alkynyl groups. The aryl and alkaryl groups can be heteroaryl and alk-heteroaryl groups. The alkyl groups may preferably a $C_1$-$C_{12}$ alkyl or a $C_5$ to $C_{12}$ cycloalkyl group. The alkenyl groups may preferably a $C_2$-$C_{12}$ alkenyl or a $C_3$ to $C_{12}$ cycloalkenyl group. The alkynyl groups may preferably a $C_2$-$C_{12}$ alkynyl or a $C_3$ to $C_{12}$ cycloalkynyl group. The aryl and alkaryl groups can be heteroaryl and alk-heteroaryl groups. The "alk" portion of the alkaryl group may be an alkyl, an alkenyl, or an alkynyl group as described here.

Preferred alkyl groups are methyl, ethyl, n-propyl, isopropyl, n-butyl, t-butyl, isobutyl, sec-butyl, cyclopropyl, cyclobutyl, cyclohexyl, (cyclohexyl)methyl, cyclopropylmethyl, homologs and isomers of, for example, n-pentyl, n-hexyl, n-heptyl, n-octyl, and the like. Preferred alkenyl groups include ethenyl, allyl, and isomers of butenyl, pentenyl, hexenyl, heptenyl, octenyl, nonenyl, decenyl cyclopropenyl, cyclobutenyl, cyclopentenyl, cyclopentadienyl, cyclohexenyl, cycloheptenyl, cycloheptadienyl, cyclooctenyl, cyclooctadienyl, and the like. Preferred alkenyl groups include acetylenyl and isomers of butynyl, pentynyl, hexynyl, heptynyl, octynyl, nonynyl, decynyl. Preferred aryl and alkaryl groups are phenyl, benzyl, and isomers of tolyl, anisyl, analinyl, naphthyl, indenyl, anthryl, pyrrolyl, pyridyl, pyrimidyl, imidazolyl, pyrazinyl, oxazolyl, isoxazolyl, thiazolyl, furyl, thienyl, imidazoyl, pyrazoyl, thiophene, N-alkylated pyrole, α-alkylated pyridine, indolyl, quinolinyl, isoquinolinyl and the like.

When RLi is $R_1R_2NLi$, the primary or secondary amines used to form the Li amide-alumina gel composition include, but are not limited to, alkylamines, dialkylamines, alkylarylamine, and diarylamines, as well as cyclic secondary amines.

The organic groups bound to nitrogen in these amines or for $R^3$ in the silyl group $Si(R^3)_3$ can include those described above for R. Preferred alkyl groups are preferably methyl, ethyl, n-propyl, isopropyl, n-butyl, trimethylsilyl, triethylsilyl, t-butyl, isobutyl, sec-butyl, homologs, and isomers of, for example, n-pentyl, n-hexyl, n-heptyl, n-octyl, and the like. Preferred aryl and alkaryl groups are phenyl, benzyl, and isomers of tolyl, anisyl, analinyl, naphthyl, indenyl, anthryl. Preferred cyclic secondary amines are pyrrolidine, piperidine, and 2,2,5,5-tetramethylpiperidine.

Any inert solvent which does not react with the lithium may be used in the preparation of the lithium reagent compositions of the invention. For example, non-reactive hydrocarbons such as hexanes or heptane or a non-reactive ether such as THF may be used. THF is generally preferred. Highly polar solvents may unfavorably compete with the reagent RX when forming the lithium reagents-porous metal oxide compositions.

Another method to generate organolithium-porous metal oxide compositions of the invention is via a carbon-hydrogen activation, meaning that the organolithium-alumina gel performs a deprotonation of a carbon atom of an added reagent to generate a new carbanion species. This organolithium exchange is typically performed at cold temperatures (e.g. about 23° C. to about −80° C.). Once the new organolithium reagent is formed, it can then be used as a nucleophile or base in a subsequent reaction with available substrates. This reaction can be performed either in a batch or flow reactor setup.

Yet another method to generate organolithium-porous metal oxide compositions of the invention is to perform an in situ metal-halogen (metal-element) exchange to transform one organolithium-porous metal oxide to a second organolithium-porous metal oxide. A single reaction vessel, either batch or flow, is charged with a haloorganic compound, RX, or any activated species with a C-Z bond (where Z can be any halide or an acidic hydrogen, etc.), can first be dissolved in THF at cold temperatures and then have organolithium-porous metal oxide added to the vessel. After the cold (i.e. between about 23° C. and about −80° C.) slurry has been well mixed for a time, the organolithium is available to react in the conventional manner with subsequently added reagents.

The organolithium-alumina gel may also be prepared by an in situ reaction using cut pieces of lithium, porous alumina gel, and alkyl halide solution (preferably, for example, hydrocarbon or ether), and evaporating off the solvent.

The organolithium reagent-porous metal oxide compositions of the invention may also be prepared by the absorption of a pre-made organolithium species in a solvent into the pores of silica gel or alumina gel under cold conditions. The excess solvent is then distilled away and the powder is vacuum dried. The product is non-pyrophoric and is preferably referred to as organolithium-silica gel or organolithium-alumina gel. The method absorbs an organolithium species into the pores of a porous metal oxide material by contacting the organolithium species with the porous material under cold conditions (e.g. about 23° C. to about −80° C.), distilling any excess solvent, and drying the resulting organolithium material.

The resulting free-flowing powders, organolithium-porous metal oxide compositions having RLi absorbed into a porous metal oxide performs all the reaction types of conventional organolithium compounds, such as nucleophilic additions to electrophiles, initiation of polymerizations, and base-catalyzed reactions, among many others. When there is no residual lithium metal in the material, the powder is also stable under nitrogen. With or without residual lithium, this material has an extended shelf life at room temperature compared to commercially available and conventional solutions of organolithium compounds that tend to aggregate, react, and decompose in the solvents they are stored inside.

Another method to generate lithium amide-porous metal oxide with the invention is to use an organolithium-porous metal oxide to deprotonate a primary or secondary amine. In a single reaction vessel, either batch or flow, a primary or secondary amine, preferably dissolved in a solvent, is charged to a stirring batch of organolithium-porous metal oxide. After the slurry is well mixed and allowed to react, any excess amine and/or solvent are decanted, removed under vacuum, or distilled at low temperature to complete the formation of a dry, free-flowing powder of lithium amide-porous metal oxide.

The lithium amide-porous metal oxide compositions ($R=R^1R^2N$) (free-flowing powders) perform the reactions known for conventional lithium amide compounds. These reactions include, but are not limited to, deprotonation of most common carbon acids including alcohols and carbonyl compounds (aldehydes and ketones). When there is no residual lithium metal in the material, the powder is also stable under nitrogen. With or without residual lithium, the material has an extended shelf life at room temperature compared to commercially available or conventional lithium amide compounds that tend to aggregate and decompose slowly. Usual methods for making these lithium amides involves the reaction of alkyl lithium species with the corresponding amine (e.g., International Patent Application Publication No. WO 03033505 by Detlef et. al.), heating a mixture of lithium with an amine above the melting point of the metal (Chiu et al., U.S. Pat. No. 5,420,322) or with small amount of isoprene as an electron carrier (Corella et al., U.S. Pat. No. 6,169,203).

As discussed above, a lithium-porous metal oxide composition, such as a lithium-alumina gel composition, may be used as a starting component for the generation of the corresponding lithium reagent composition of the invention, e.g. the corresponding organolithium-alumina gel or lithium amide-alumina gel composition. As a more specific example of the preparation of such a corresponding composition, the lithium-alumina gel is cooled to temperatures ranging from about −80° C. to about 0° C. and stirred for several minutes. To the stirring lithium-alumina gel, a haloorganic, either in its neat form or in solution of a non-reactive hydrocarbon or ether solvent such as tetrahydrofuran (THF), is slowly added. The reaction mixture is stirred for several hours at cold temperatures. Any excess unreacted haloorganic, or solvent, may be distilled off under vacuum while the system temperature is raised to room temperature. The strength (reaction equivalents per gram) of the final organolithium-alumina gel composition is measured by performing the nucleophilic addition to an electrophile in a separate reaction setup. In the case of butyl bromide, the reaction appears to be:

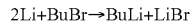

Using the pure compound densities of LiBr (3.464 g/cm$^3$) and BuLi (0.67 g/cm$^3$), the volume per mole of products is 25.1 cm$^3$ for LiBr and 95.5 cm$^3$ for BuLi for a total of 120.6 cm$^3$/mole. The void volume in alumina gel (from mercury porosimetry) is 1.56 cm$^3$/g. Assuming that the products fit in the pores without increasing the volume, then for a sample of alumina gel of mass 8.0 g, there is a maximum of 12.5 cm$^3$ of void space. That means that 8.0 g of AG could accommodate 12.5/120.6=0.110 moles of reaction, which would require 1.53 grams of Li. This would correspond to a Li loading of (1.53/9.53)×100=16.0 wt %. The loading of BuLi would then be 0.110/9.53=0.0115 moles/g lithium-alumina gel or 11.5 mmol/g lithium-alumina gel.

The maximum loading of the organolithium-alumina gel for two example systems, butyllithium-alumina gel and methyllithium-alumina gel, are shown in Table 1 below on the basis of 10 g total weight of lithium-alumina gel used:

TABLE 1

Maximum Loadings

| For BuLi: 2Li + BuBr --> BuLi + LiBr | |
|---|---|
| Loading of Lithium Alumina Gel | 15.0% |
| Total Available Volume | 13.26 cc |
| Volume per Mole of BuLi Produced | 95.52 cc/mol |
| Volume per Mole of LiBr Produced | 25.12 cc/mol |
| Reaction Potential in Alumina (mol) | 0.11 moles |
| Amount of Li to Complete Reaction (g) | 1.54 g |
| Volume of BuLi Produced | 10.50 cc |
| Volume of LiBr Produced | 2.76 cc |
| Amount of BuLi in Alumina | 10.99 mmol/g of Li-AG |
| For MeLi: 2Li + MeI --> MeLi + LiI | |
| Loading of Lithium Alumina Gel | 17.2% |
| Total Available Volume | 12.92 cc |
| Volume per Mole of MeLi Produced | 66.67 cc/mol |
| Volume per Mole of LiI Produced | 38.35 cc/mol |
| Reaction Potential in Alumina (mol) | 0.12 moles |
| Amount of Li to Complete Reaction (g) | 1.72 g |
| Volume of MeLi Produced | 8.20 cc |
| Volume of LiI Produced | 4.72 cc |
| Amount of MeLi in Alumina | 12.30 mmol/g of Li-AG |

The amount of lithium metal loading is dependent upon the pore size and pore density of the actual porous metal oxide used. Typically, the lithium metal may be present in the compositions of the invention up to about 40% by weight. Preferably, the amount of metal ranges from 20% to 40% by weight, if the material is being used for typical reductions and in situ lithiation applications. The preferred loading to generate organolithium-porous metal oxide and lithium amide-alumina gel compositions ranges from 10% to 20% lithium by weight. In the lithium-porous metal oxide compositions of the invention, loadings above about 40% by weight can result in some free metal remaining on the surface of the porous metal oxide.

Various additives known to stabilize organo lithium reagents may also be used with the lithium reagent-porous metal oxides. These include but are limited to stabilizers, such as tetramethyl ethylenediamine (TMEDA), diazabicycloundecane (DBU), sparteine (see Tsumaki et al., U.S. Pat. No. 6,024,897), may also be added to further increase the stability of the carbanions in these solids. For example, stabilized versions of organolithium species can be made by using tetramethylethylenediamine (TMEDA) as an additive to the synthesis. Typically, for every two (2) moles of lithium, one (1) mole of haloorganic and one (1) mole of TMEDA is used to make organolithium-TMEDA-porous metal oxide. The molecular structure of TMEDA corresponds to one molecule of 1,2-diaminoethane alkylated with two methyl groups on each of the two amine nitrogen atoms. TMEDA, or other tertiary amine stabilizers, can be used as additives to help stabilize these reagents by virtue of the tertiary nitrogen coordination with the lithium cation. Potentially, this ion complexation expands the effective radius and reduces the electrophilicity of the lithium cation, isolating it from the carbanion portion and thus limiting its capacity for beta-hydride abstraction from the alkyl carbanion. This mode of stabilization is also thought to enhance the carbanion's availability for reaction with externally added reagents.

Use of Lithium- and Lithium Reagent-Porous Metal Oxide Compositions

The lithium-porous metal oxide compositions and the lithium reagent-porous metal oxide compositions of the invention may be used for the same reactions as is lithium metal, organolithium reagents and lithium amide reagents. These include, but are not limited to nucleophilic addition reactions, polymerization reactions, and base-catalyzed reactions. Table 2 provides an exemplary list of such reactions. The compositions of the invention, however, have the advantage of being free flowing powders and more storage stable.

TABLE 2

| Reagent | Use | Reaction example | Reference |
|---|---|---|---|
| RLi-AG | (1) Nucleophilic additions to carbon centered electrophile | $RLi + R_2CO \rightarrow R_3COLi$<br>$RLi + CO_2 \rightarrow RCO_2Li$ | Wu, G. Huang, M. *Chem. Rev.* 2006, 106, 2596. |
| | (2) Preparation of organocuprate or Gilman's reagent | $2RLi + CuX \rightarrow R_2CuLi + LiX$ | Walborsky, H. M.; Ronman, P. J. *Org. Chem.*, 1978, 43, 731 |
| | (3) Preparation of organophosphorous, organosulfur, organoboron, organotin compounds from appropriate electrophiles | $RLi + PX_3 \rightarrow PR_3 + 3LiX$<br>$RLi + RSCN \rightarrow RSR +$ LiCN | |
| | (4) Preparation of lithium amides such as LDA and LiHMDS | $RLi + R_2NH \rightarrow R_2NLi + RH$ | House et al., *J. Org. Chem.*, 1978, 43, 700. |
| | (5) Directed ortho-lithiation and subsequent quenching with electrophiles. | | |
| | (6) Preparation of enolates and other deprotonations (e.g., preparation of other organolithium by Li—H exchange) | nBuLi + toluene →<br>BnLi + nBuH | Eisch, J. J. *Organomet.* Synth. 1981, 2, 95. |
| | (7) Initiator for anionic polymerizations | | |
| | (8) Generation of Ylides in Wittig reaction | $R_3PCH_3Br \rightarrow R_3P{=}CH_2$ | Maercker, A. *Org. React.* 1965, 14, 270. |
| | (9) Generation of carbene | $R_2CX_2 \rightarrow R_2C{:}$ | Xu, L.; Tao, F.; Yu, T. *Tetrahedron Lett.* 1985, 26, 4231. |
| | (10) Isotopic labelling (e.g., D, T) | $RLi + D_2O \rightarrow RD + LiOD$ | |
| | (11) Shapiro reaction | | |
| $R_2NLi$-AG | (1) As non-nucleophilic base such as LDA | Elimination (e.g., β-H), sigmatropic carbanion rearrangements, generation of carbanions, reductive cleavage of ethers, ortholithiations, aldol reactions, anionic polymerizations | Lochmann et al, *J. Organometallic Chem*, 1979, 123. |
| Li-AG | (1) Preparing organolithium compounds by halogen-metal exchange or reductive cleavage of C—O, C—S or C—P bonds. | $RX + 2Li \rightarrow LiX + RLi$<br>$RSR + Li \rightarrow RLi + RSLi$ | Main Group Metals in Organic Synthesis by Tomooka, K,; Ito, M. 2005, Wiley-Verlag, GmbH |
| | (2) Reductions of cabonyls, aromatics (Birch reduction) | $R_2CO \rightarrow R_2CHOH$ | |
| | (3) Generation of reactive intermediates such as arenides, | $NpH + Li \rightarrow Np(-)Li(+)$ | |

Additionally, as solid state reagents, the lithium-porous metal oxide compositions and the lithium reagent-porous metal oxide compositions of the invention may be used for reaction purposes in several ways. The simplest mode is a conventional batch reaction in which the solid reagent is stirred in a slurry with a solution of substrate(s). Here, the principle advantages over commercially available solid lithium preparations or solutions of organolithium or lithium amide reagents are in (a) ease of solids handling and (b) minimization of organic solvent usage in reaction, quenching, and workup procedures. In favorable cases, when solid acids are included in the slurry, direct isolation of the organic solution containing only neutralized product is facilitated by the affinity of the solid oxide gel (e.g. alumina or silica) for ionic byproducts which therefore do not have to be removed via separate organic/aqueous partition and washing steps.

A second mode of use is in a process flow reactor, (e.g. a column flow reactor), in which solutions of reaction substrate percolate through a packed bed of the solid lithium alumina gel, organolithium-solid oxide, or lithium amide-solid oxide reagent. With flow process reactors, or continuous flow reactors, fresh reactant solution is continuously added to the reactor solid-state reagent. Reaction products are continuously removed while the waste is either left bound to the supported reagent or co-eluted with desired products. The advantages of using a flow process reactor are numerous. For example, the reactor insures efficient use of all the reagent material, only having to be shut down when its reaction capacity is fully exhausted. The result is a process both more productive and more efficient in gel material and in solvent than a conventional batch reaction. An example of a flow process reactor is a fixed-bed flow reactor in which a liquid solution of reaction substrate is percolated through a column of solid reagent, such as for example an organolithium-alumina gel, with direct collection of the product solution at the column's exit. While virtually any type of reaction process and reactor may be used for the reactions described herein, a flow process reactor, such as a fixed-bed flow column reactor, is the preferred reactor type for the reactions of the invention.

Depending on choice of solvent and the nature of the organic portions, organolithium or lithium amide species formed via reaction of haloorganic or organic amines with lithium-alumina gel may be soluble enough to be eluted, providing flexible access to freshly prepared solutions of pure organolithium or lithium amide reagents. Alternatively, when a targeted organolithium species is expected to be particularly unstable or short-lived, its electrophilic partner (e.g. proton source, ketone, etc.) may be directly included in solid form in the bed of the packed column, again providing quenched neutral product in pure form at the column exit.

Alternatively, a sequential reaction scheme is possible, in which a solid oxide-bound organolithium or lithium amide formed in situ from the lithium-alumina gel is then allowed to react with a solution of substrate, fed in the same or different solvent, and forming product that is subsequently eluted from the column. This method is thus advantageous in terms of (a) efficient usage of the lithium's reactivity, (b) safety, since the eluted product is free of lithium metal, (c) in applications that call for the intermediacy of unstable organolithium species, and (d) in allowing sequential formation and reaction of supported reactants, followed by their elution from polar/ionic byproducts and unreacted lithium metal.

EXAMPLES

Example 1

Preparation of Li-AG (10% w/w)

In a He glove box 3.16 g of lithium ribbon (1.425 g/ft) was weighed out and cut into small pieces and coated thoroughly with 28.4 g Alumina gel (AG) before putting into the steel reactor. The steel reactor was heated to 100° C. for 6 hours, 165° C. for overnight, 182° C. for 8 hours and 190° C. for overnight. The steel reactor was cooled and transferred into the glovebox. A small representative sample of 76.7 mg was tested for $H_2$ evolution with water. The amount of $H_2$ collected came out to be equivalent to 9.2% of Li. Variations in the amount of lithium loadings have been prepared ranging from 5 wt % to 40 wt % by varying the stoichiometric ratio of lithium metal to porous alumina gel.

Example 2

Preparation of Organolithium Species Stabilized Inside Lithium-Alumina Gel

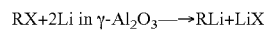

$$RX + 2Li \text{ in } \gamma\text{-}Al_2O_3 \rightarrow RLi + LiX$$

where RX can be halides (chloride, bromide or iodides) of aliphatic (methyl, butyl etc), aromatic (Phenyl), benzylic, allylic, homoallylic, propargyllic, sec-alkyl, tert alkyl or neopentyl groups.

1 g 10% (14 mmole Li) Li in γ-$Al_2O_3$ was taken in a round bottom flask and chilled in a dry ice-acetone bath at −78° C. followed by dropwise addition of methyl iodide (2 mL) (neat) into the stirring slurry. The reaction was stirred cold for 2 hours. The excess methyl iodide was distilled off after the addition was complete and the mixture reached room temperature. A small amount of ethane and I2 was produced during this preparation, but this Wurtz coupled product could be minimized by maintaining the cold temperature for a longer duration. The strength of MeLi in alumina was determined through the nucleophilic addition reaction with excess benzophenone. Between various runs, the loading of MeLi in alumina (prepared from 10-25% Li in γ-$Al_2O_3$) was determined to be between 3-7 mmol/g. For stoichiometric reactions of organolithium and benzophenone the nucleophilic addition product yield varied between 75%-90% along with traces of ortholithiation product.

$PhCH_2Li$, n-BuLi, allyllithium and homoallyllithium were prepared using the same procedure and tested for reactivity with enzophenone.

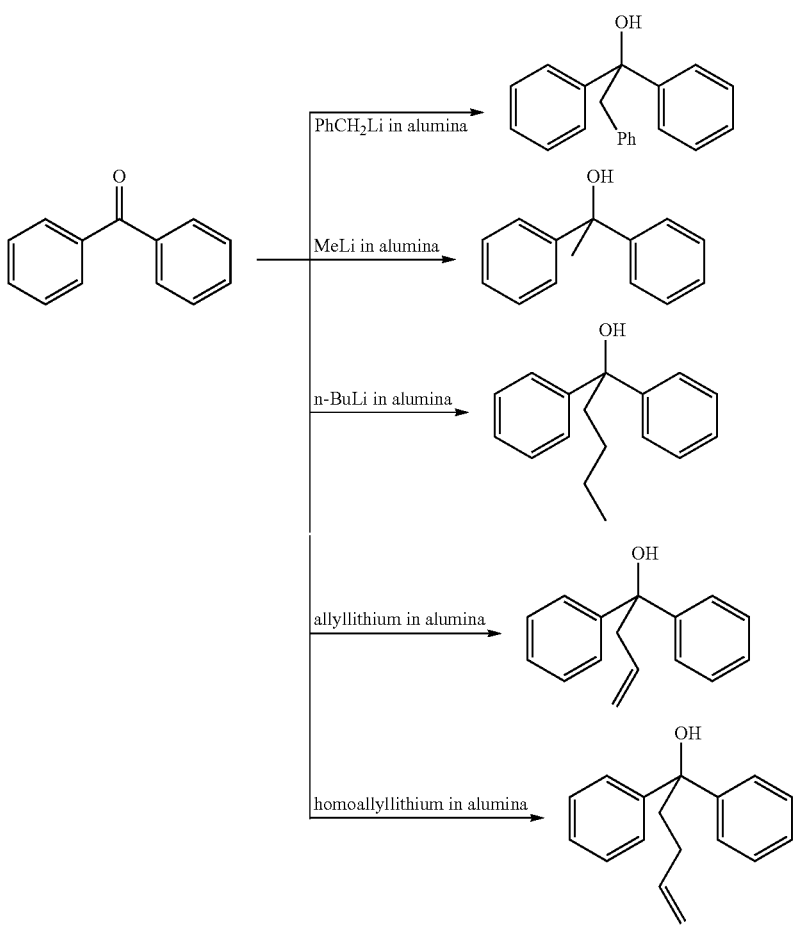

Example 3

Preparation of Organolithium-Alumina Gel with TMEDA Stabilizer

In a flask containing 2 g of Li-AG (25% Li by weight) a mixture of 2 g TMEDA, 3 g n-butyl bromide in 20 mL of pentane was distilled in and stirred at −80 C for 3 hours, followed by a replacement by a dry ice bath at −40° C. and stirring the reaction overnight till it reached room temperature. The solvents were removed under vacuum to afford a grey free flowing powder. 200 mg of this material was reacted with 1.1 mmole (200 mg) of PhCOPh to afford butyl diphenyl alcohol in 60% yield. FIG. 1A shows the $^1$H NMR of the butyldiphenyl alcohol product.

Figure 1B:
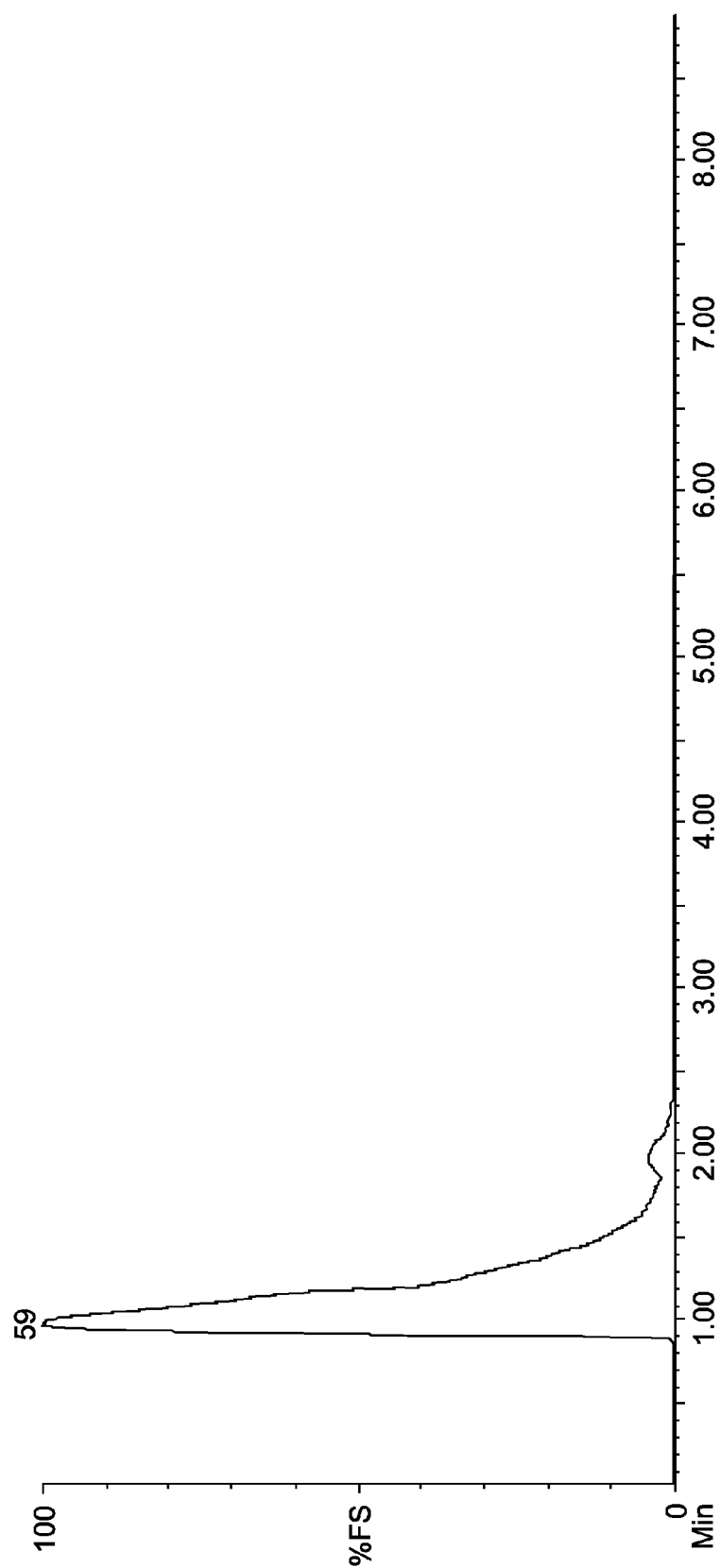
Figure 1C:
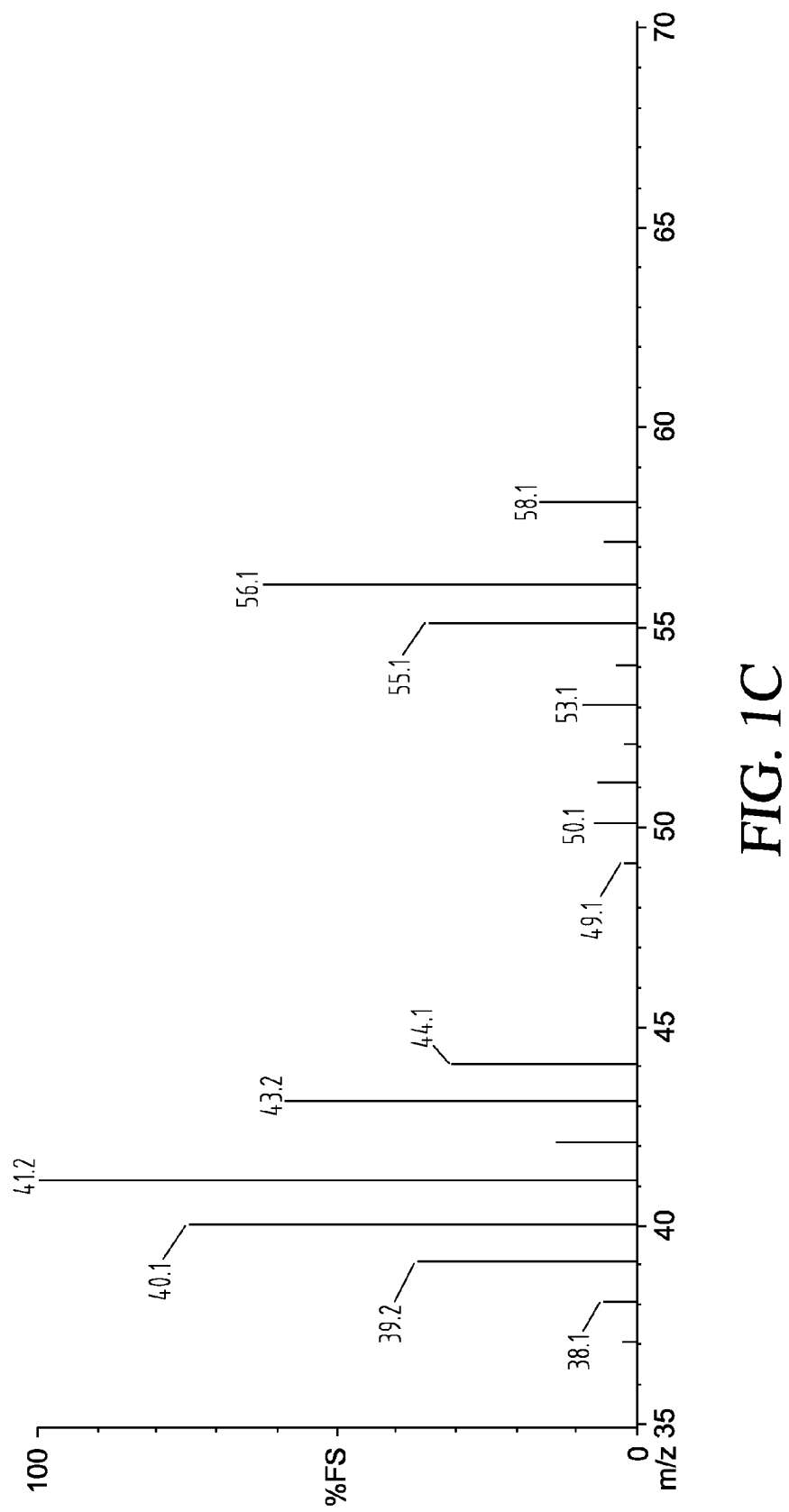

The presence of the butyl anion was also confirmed by running a gas evolution reaction of this material with water and analyzing the gas by GC-MS that indicated formation of butane (MW=58) according to the following reaction. See FIGS. 1A-1B.

$$C_4H_9Li + H_2O \rightarrow C_4H_{10} + LiOH$$

Example 4

Generation of Organo Lithium-Porous Metal Oxide Composition and One Pot Nucleophilic Addition to Ketone

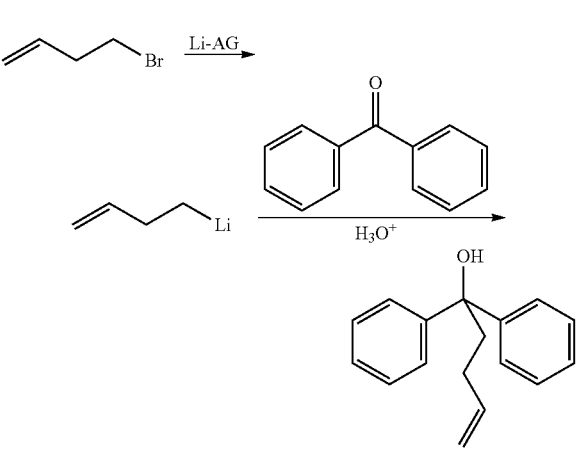

1.5 mmole of homoallylbromide (195 mg) was dissolved in 5 mL dry and distilled THF and this solution was cooled to −78° C. To this cooled solution 0.5 g of Li in γ-Al$_2$O$_3$, (8-12% w/w, 7-10 mmole of Li), was added through a solid addition tube for a period of 15 minute. The slurry was stirred for 30 minutes under the same cold condition. To the cold stirring slurry, 1 mmole of benzophenone (182 mg) dissolved in 3 mL THF was added over a period of 15 minutes. The reaction was warmed to room temperature slowly (6 h), followed by quenching with cold water and extraction with EtOAc. The organic layer was evaporated under nitrogen yielding 200 mg (85%) of oily residue.

Figure 2:
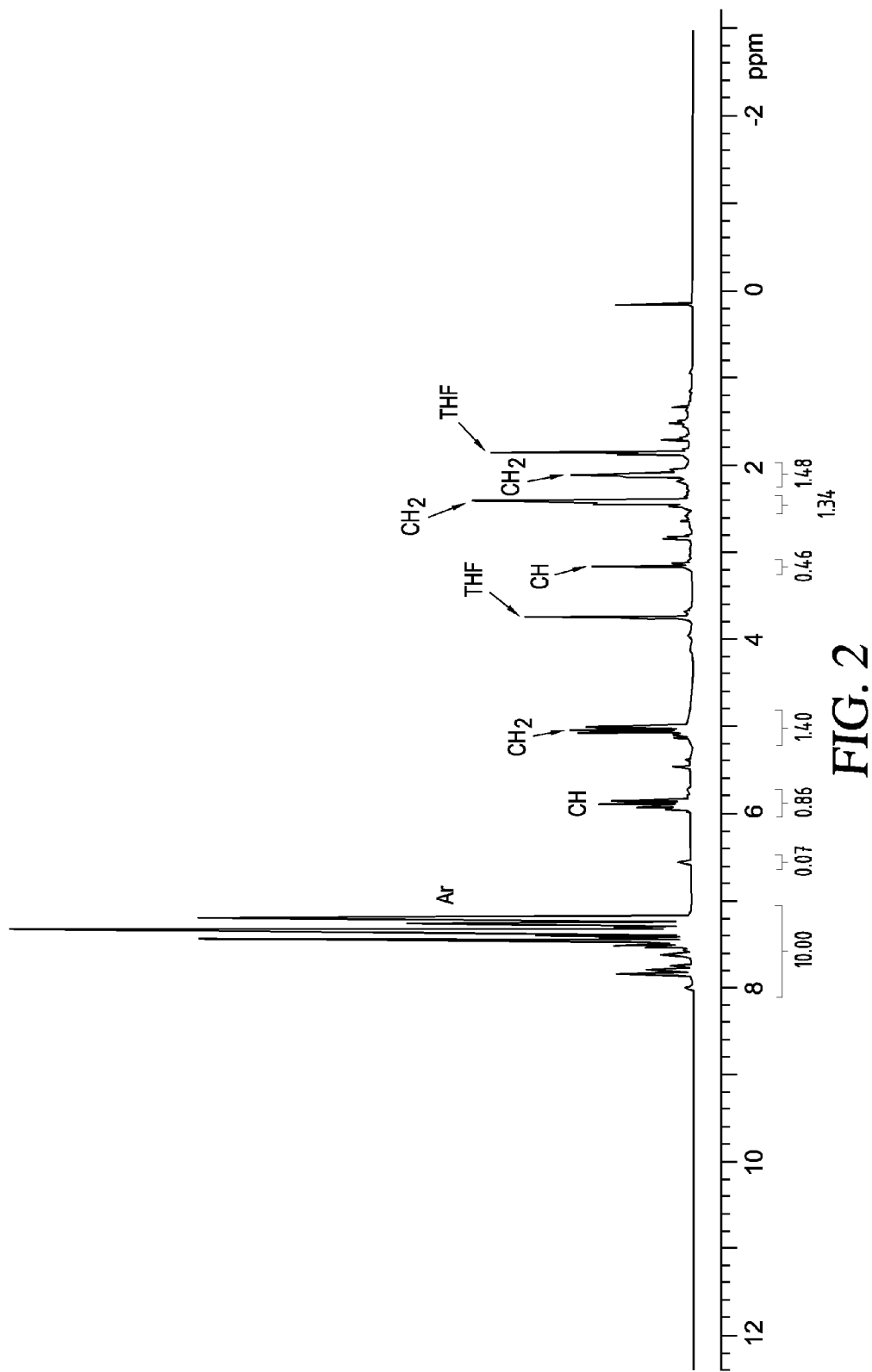
FIG. 2 shows a $^1H$ NMR spectrum representative of the results of Example 4.

FIG. 2 shows the $^1$H NMR ($\delta$ in ppm) of the product $^1$H homoallyldiphenyl methyl alcohol with peaks as follows: 7.2-7.8 (m, 10H), 5.8-6.0 (m, 1H), 5.0-5.2 (m, 2H), 2.4-2.6 (m, 2H), 2.05-2.15 (m, 2H).

Example 5

Generation of Organolithium (Lithium Amide) from the Reaction of a Secondary Amine with Lithium in Alumina Gel 1 g of lithium-alumina gel (loaded with 25 wt. % Li) was reacted with dimethyl amine (~4 mL) to afford a deep blue solution at –60° C. Upon gradual warming to room temperature, the solution mixture began to bubble presumably due to formation of hydrogen gas. On standing at room temperature for another 1 h, the blue color of the solution completely disappeared. Excess unreacted dimethyl amine was evaporated under vacuum and the resulting solid was weighed. 1.35 g Me$_2$NLi-alumina gel was obtained (~40% yield with respect to amount of Li used).

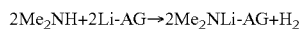

2Me$_2$NH+2Li-AG→2Me$_2$NLi-AG+H$_2$

Comparative Example 1

Attempt to Generate Lithium Dimethylamide from the Reaction of a Secondary Amine with Lithium Metal 30 mg of fresh and finely divided lithium metal was taken in a round bottom flask equipped with a vacuum stopper, to which Me$_2$NH was condensed. The reaction vessel was initially kept at –60° C. for several minutes and then was gradually warmed up to room temperature and maintained at that temperature overnight with a pressure gauge. No coloration of the Me$_2$NH or H$_2$ gas evolution was observed.

Comparative Example 2

Attempt to Generate Lithium Dimethylamide from the Reaction of a Secondary Amine with Lithium Metal in the Presence of Alumina Gel 30 mg of porous alumina gel was combined with 20 mg of finely divided lithium metal in a flask equipped with a vacuum stopper, and to this mixture Me$_2$NH was condensed. The reaction vessel was initially kept cool and was then gradually brought to room temperature and was maintained there for 2 h. No coloration of the Me$_2$NH or H$_2$ gas evolution was observed.

Comparative Examples 1 and 2 demonstrate that lithium metal, alone or in the presence of alumina, does not form the lithium amide starting from dimethyl amine.

Example 6

Continuous Flow Reaction of Organolithium in a Column

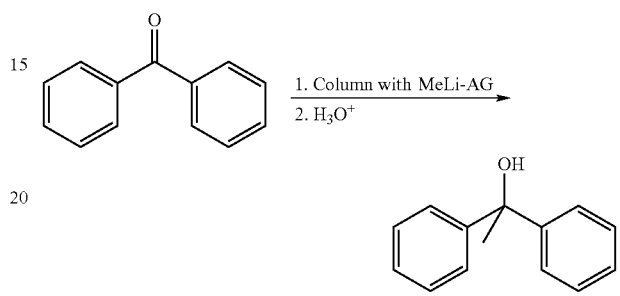

1 mmole (182 mg) of benzophenone dissolved in 5 mL of THF was passed through a cold-jacketed column (–40° C.) packed with MeLi in alumina (5 mM, 2 g) for a period of 1 h. The column was washed with excess THF and the collected product was subjected to quenching in cold water, followed by extraction in EtOAc and evaporation of the organic layer to afford an oily liquid (185 mg) in 92% crude yield (containing traces of ortholithiation product). The pure alcohol was isolated by reversed phase (C$_{18}$) column chromatography by eluting with MeOH (73%).

Example 7

Reduction of a Ketone Using Lithium-Alumina Gel

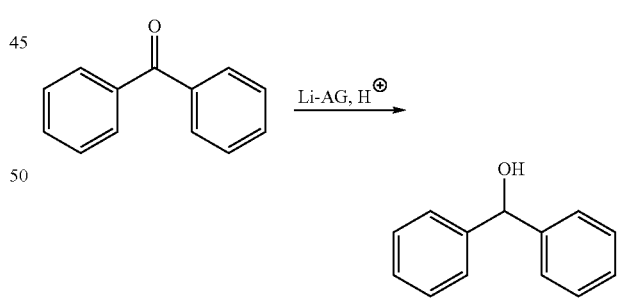

Figure 3A:
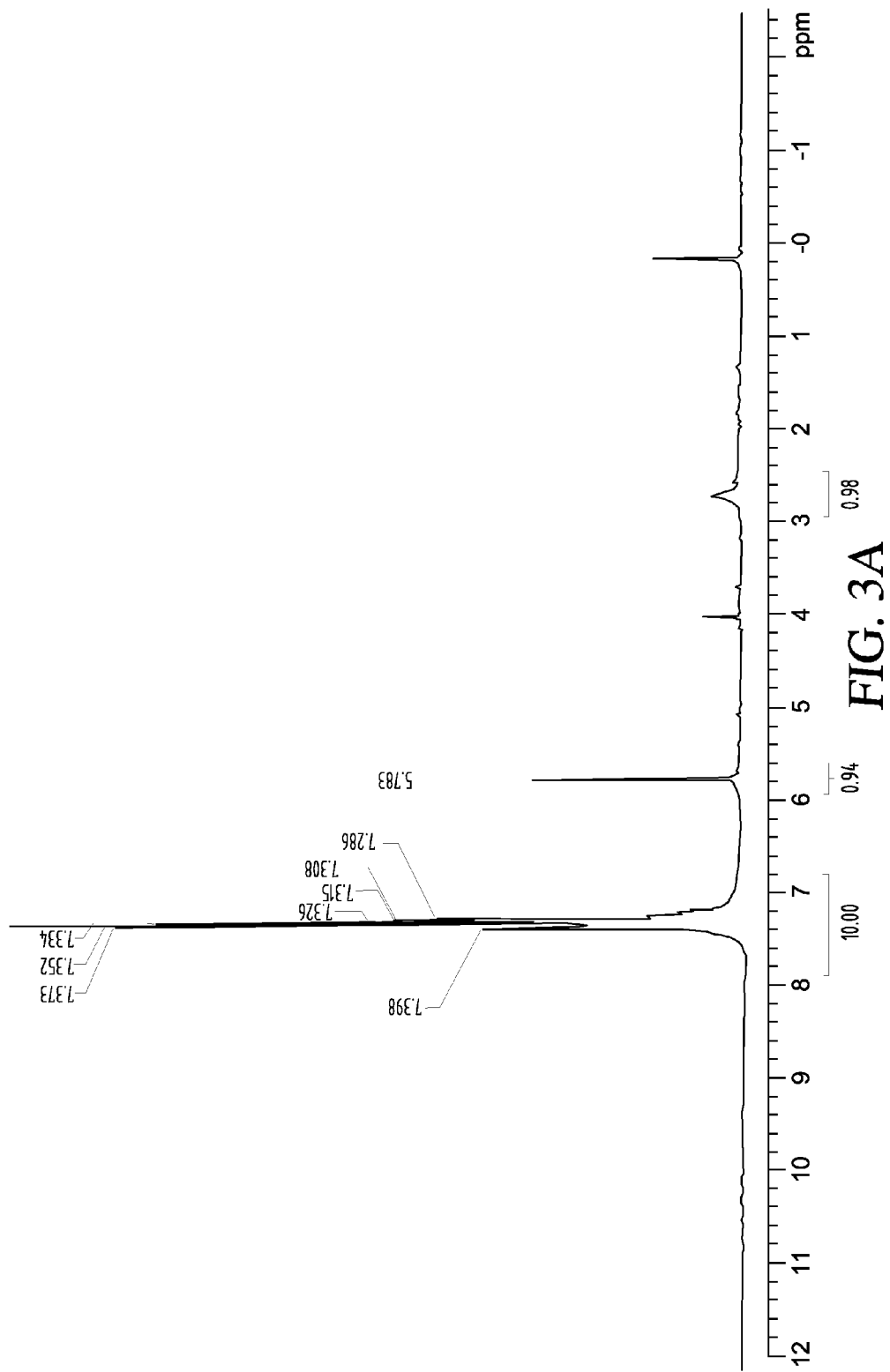
FIGS. 3A-3C show $^1H$ NMR, $^{13}C$ NMR, and ESI-MS spectra representative of the results of Example 7.
Figure 3B:
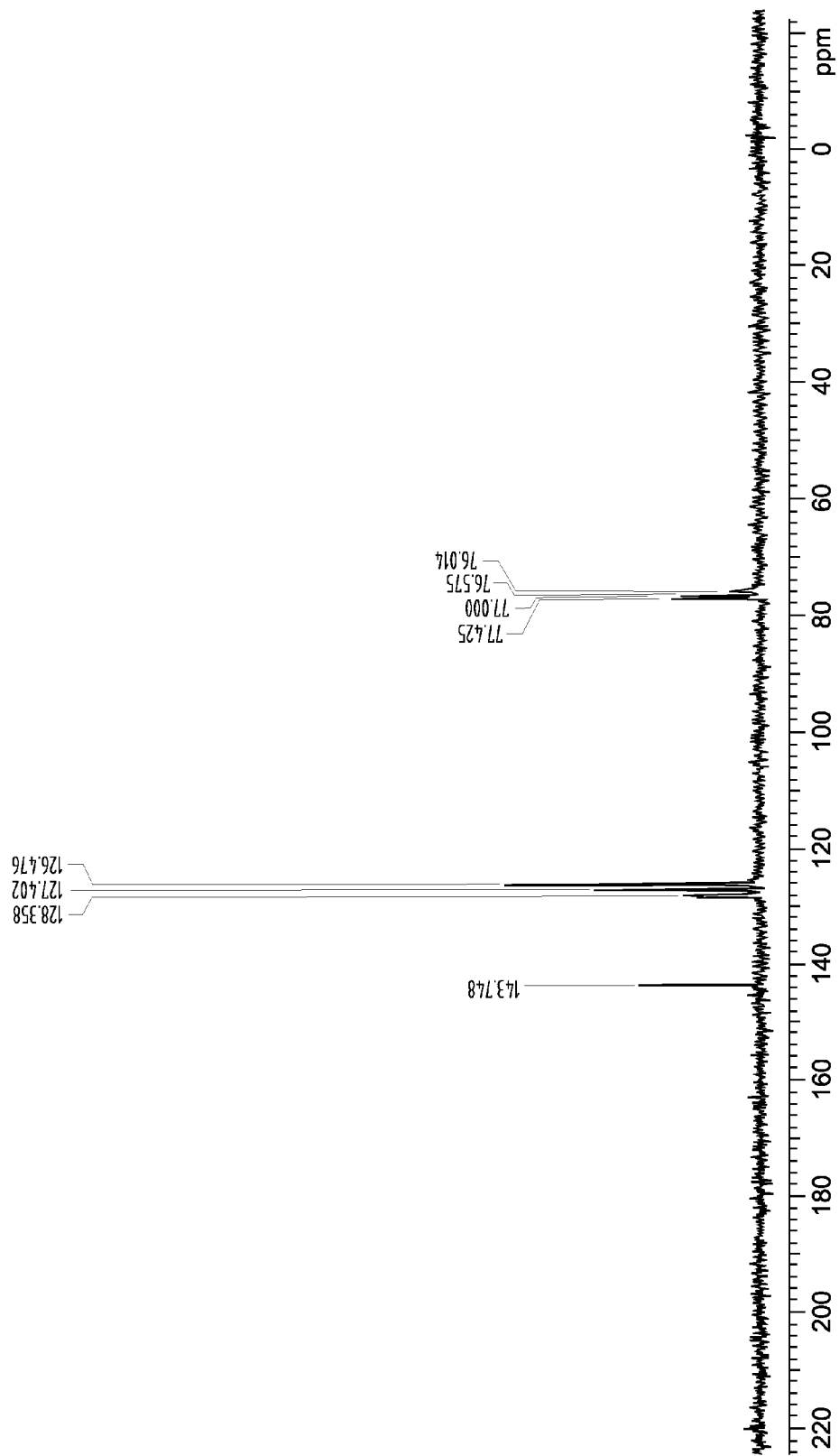
Figure 3C:
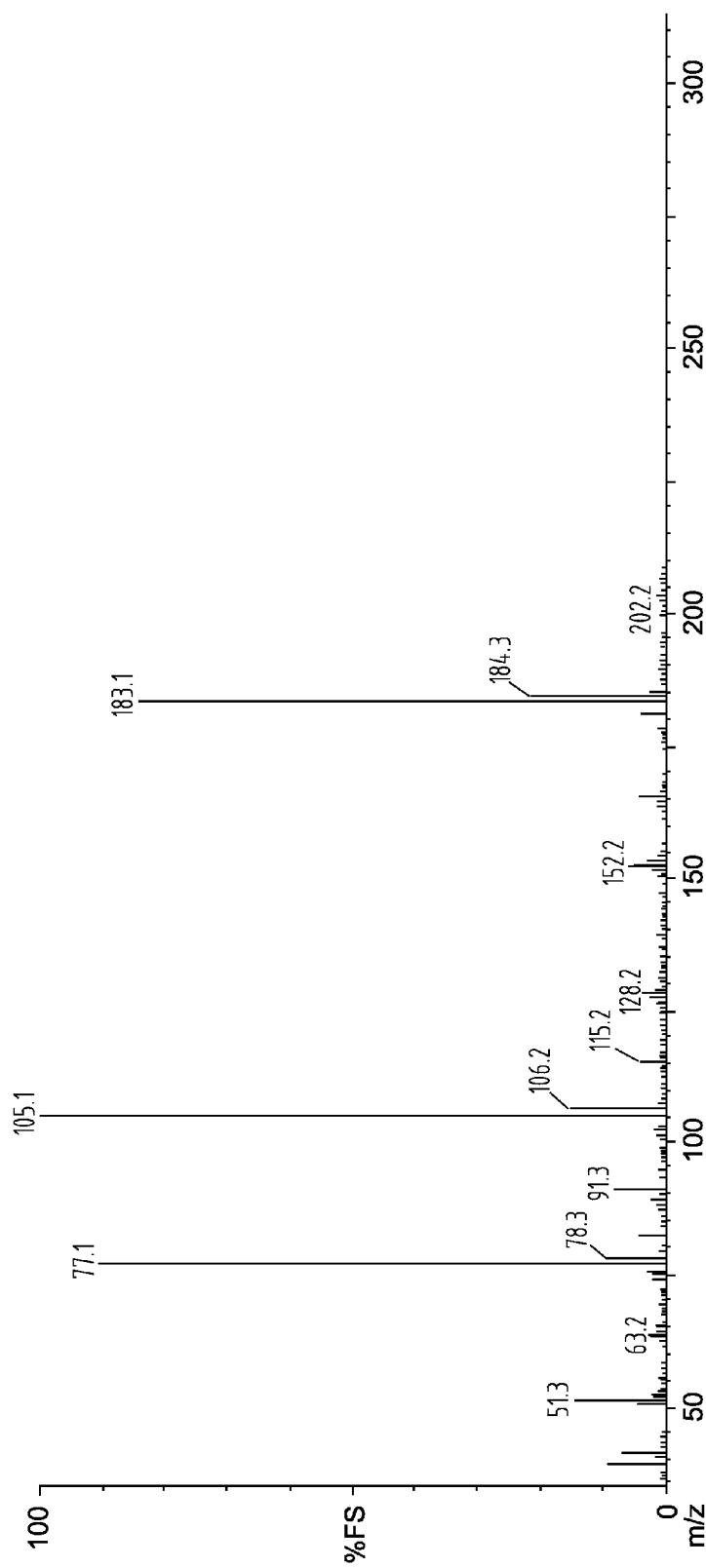

1 mmole (182 mg) of benzophenone dissolved in 5 mL THF was stirred with 0.5 g of 12% Li-AG and solid state proton sources such as NH$_4$Cl, (NH$_4$)$_2$HPO$_4$, or dropwise addition of glacial AcOH at room temperature after a deep blue colored solution is produced. The color of the reaction vessel gradually fades and becomes grey at the end indicating complete consumption of lithium. The reaction mixture was filtered, the solids washed with hexane, and the solvent was removed from the combined organic solutions under vacuum to obtain a white solid corresponding to diphenyl methanol as confirmed by $^1$H, $^{13}$C NMR and ESI-MS. See FIGS. 3A-3C.

Example 8

Preparation of RLi-AG from a Three Component Reaction of RX, Lithium Metal, and Alumina Gel In a flask containing 2 g of calcined alumina gel and 202 mg of lithium ribbon cut into 5 small pieces were massed out and equipped with a glass coated magnetic stir bar and a rubber septum. This flask was chilled to −10° C. for 10 minutes in a cryobath. To this flask, 40 mL of dry hexane was added followed by an additional 200 μL of n-BuBr. The reaction was stirred for 30 minutes causing the lithium pieces to turn shiny. An additional 500 μL of n-BuBr was added for the next 1 hr followed by an additional 800 μL of n-BuBr for the next 20 minutes. The reaction mixture was stirred in cold for another 3 hr until all of the lithium and organic derivative was incorporated into the alumina gel. At this point, the reaction was stopped and maintained cold and the hexane layer was analyzed for n-BuLi.

212.5 mg of diphenyl acetic acid solution in THF was placed in a round bottom flask to which the n-BuLi in hexane layer from the reaction mixture was added. 15.5 mL of hexane solution was needed to produce a color change of the diphenylacetic acid, which corresponds to 2 mmol of n-BuLi. Based on this finding, the total hexane layer should have 5.16 mmol of n-BuLi making the n-BuLi absorbed in the solid alumina gel should equal 8.84 mmol.

Figure 4:
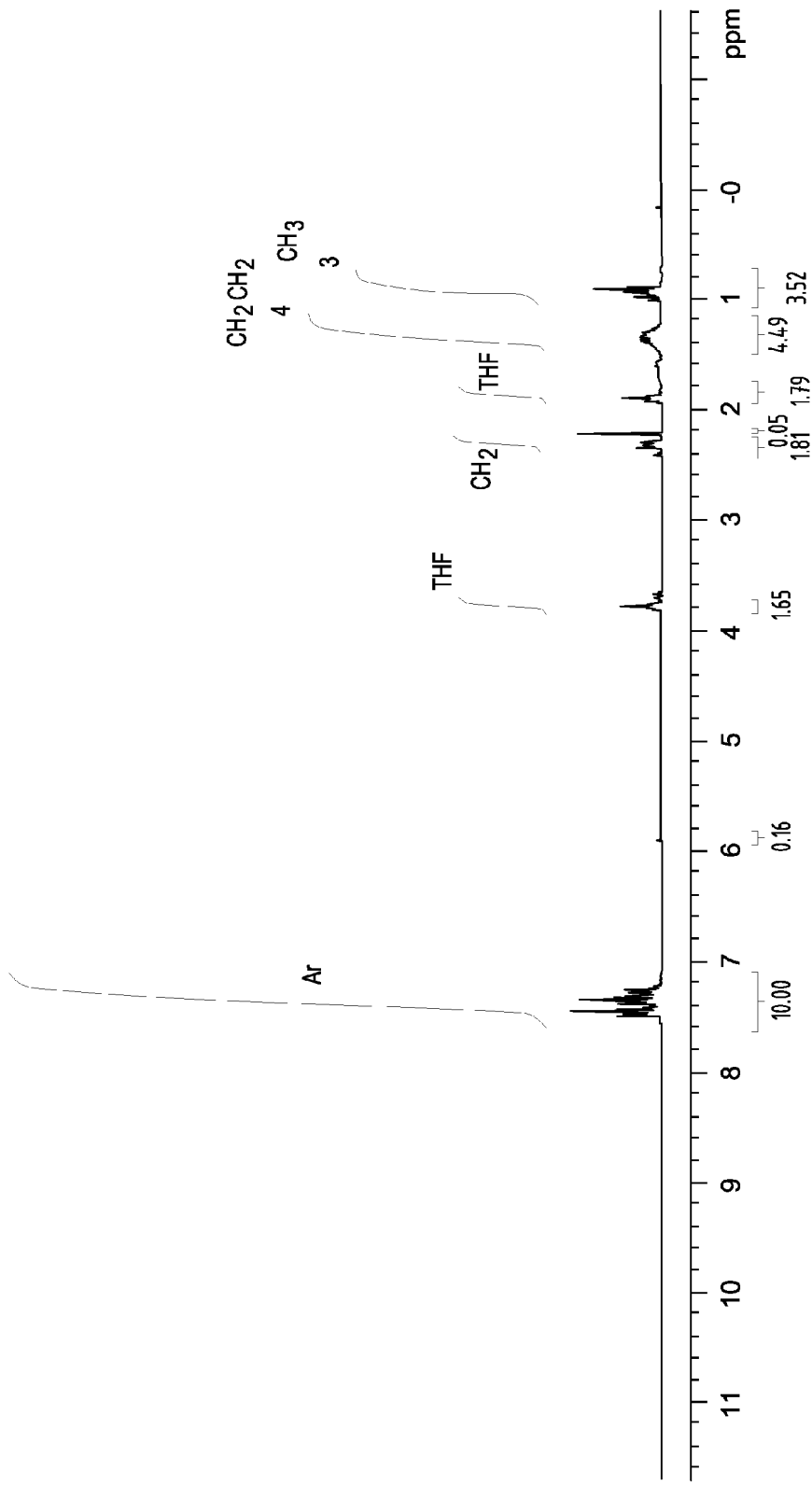
FIG. 4 shows an $^1H$ NMR spectra representative of the results of Example Example 8.

609 mg of BuLiAG when reacted with 1 mmol of PhCOPh (182 mg) afforded nearly 90% conversion of the desired nucleophilic adduct by $^1$H NMR. δ (ppm): 7.2-7.5 (m, 10H), 2.3 (t, 2H), 1.4 (m, 4H), 0.95 (t, 3H). (See FIG. 4).

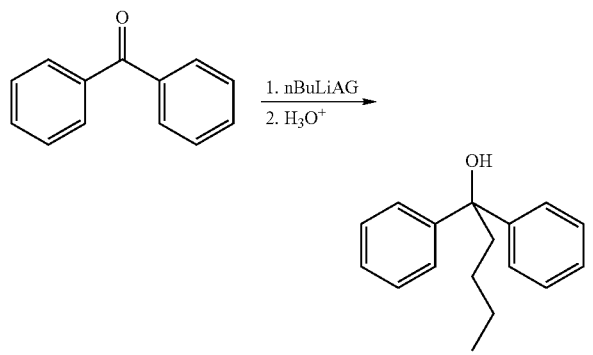

Example 9

Preparation of Vinyllithium from Reductive Cleavage of Ethylvinylether

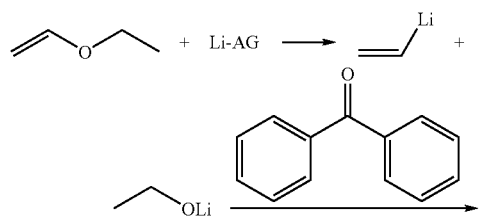

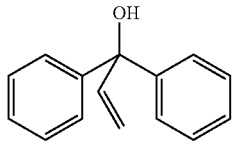

500 mg Li-AG (12% w/w) was weighed out in a round bottom flask equipped with a magnetic stirbar and rubber septum. To this flask, 2 mL ethyl vinyl ether was added via a syringe at −40° C. After stirring the mixture at −40° C. for 20 minutes a solution of 1 mmol benzophenone in 3 mL ethylvinylether was added to the reaction mixture dropwise. The rate of addition was maintained in such a way that it was not allowed for the blue color of benzoketyl radical anion to persist (waited till the blue color disappeared after each drop). The total addition took about an hour after this time the color of the reaction started to turn red. The reaction was stirred for additional 1 hour in cold and then brought to room temperature before quenching with water. The organic layer was extracted with ether (multiple times), dried and the crude yield was recorded to be 200 mg (57%).

Figure 5A:
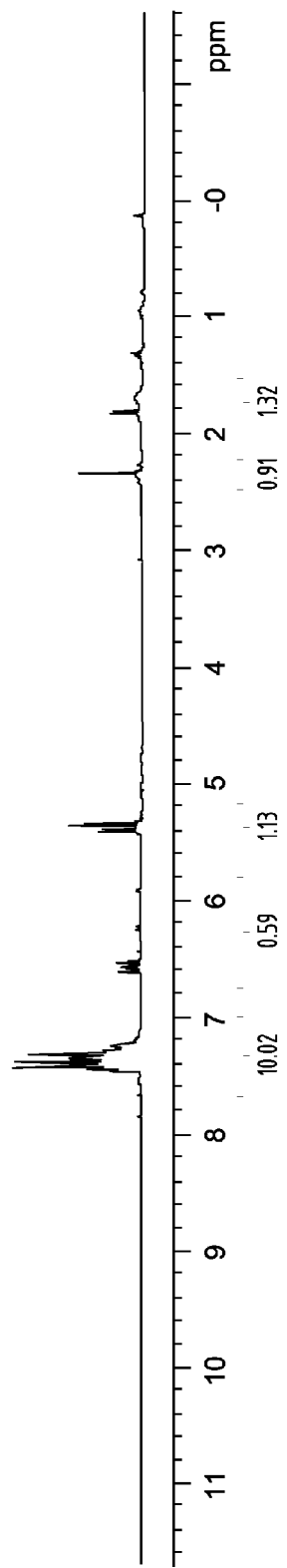
FIGS. 5A-5C show $^1H$ NMR, GC-MS, and $^{13}C$ NMR spectra representative of the results of Example 9.

The $^1$H NMR (FIG. 5A) of the crude mixture also indicates conversion of 54%, and shows $^1$H NMR (δ in ppm) peaks as follows: 2.27 (br, 1H), 5.32 (d, 1H), 5.33 (d, 1H), 6.51 (dd, 1H), 7.2-7.5 (m, 10H).

Figure 5B:
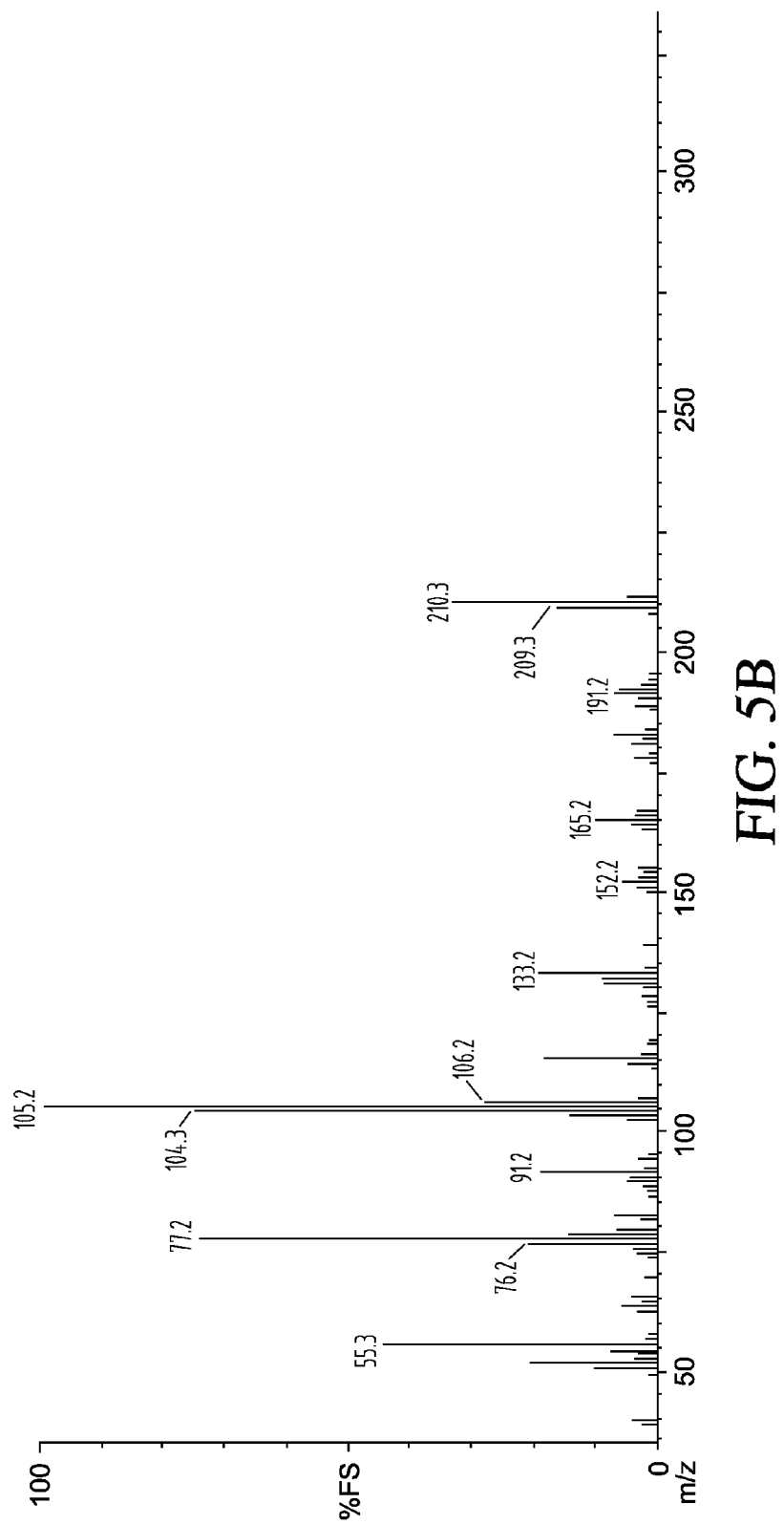

The GC-MS (FIG. 5B) indicates formation of nucleophilic adduct corresponding to its m/z peak at 210.

Figure 5C:
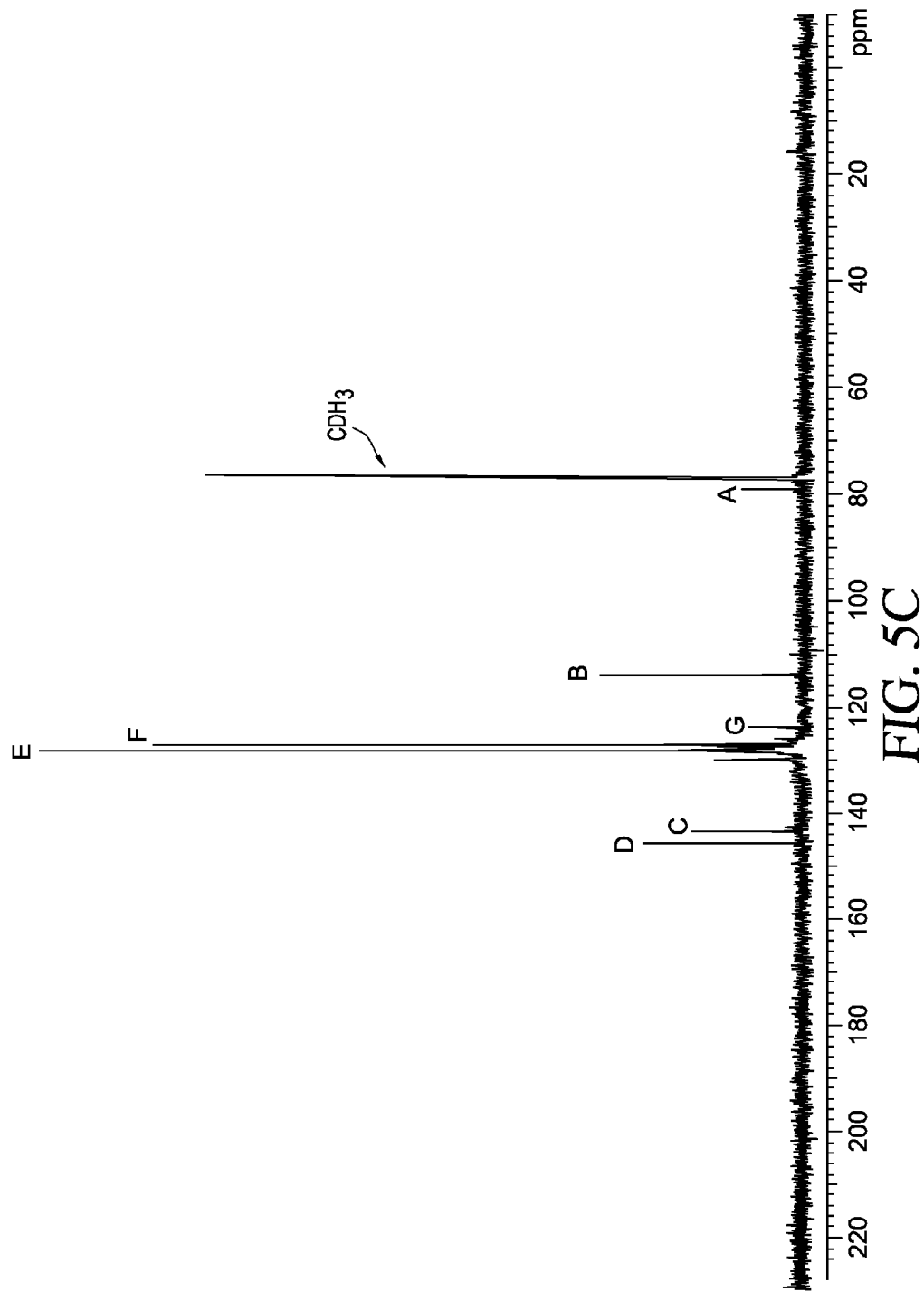

$^{13}$C NMR in CDCl$_3$ (δ in ppm) (FIG. 5C) shows peaks at 145.7, 143.5, 128.6, 127.9, 126.9, 114, 79.4

The claimed invention is:

1. A lithium reagent-porous oxide composition consisting essentially of RLi absorbed into a porous oxide, wherein:
   R is an alkyl group, an alkenyl group, an alkynyl group, an aryl group, an alkaryl group, or an NR$^1$R$^2$ group;
   R$^1$ is an alkyl group, an alkenyl group, an alkynyl group, an aryl group, an alkaryl group or an Si(R$^3$)$_3$ group;
   R$^2$ is hydrogen, an alkyl group, an alkenyl group, an alkynyl group, an aryl group, an alkaryl group, or an Si(R$^3$)$_3$ group; and
   R$^3$ is an alkyl group, an alkenyl group, an alkynyl group, an aryl group, or an alkaryl group.

2. The lithium reagent-porous oxide composition of claim 1, wherein R is selected from the group consisting of methyl, ethyl, n-propyl, isopropyl, n-butyl, t-butyl, isobutyl, sec-butyl, ethenyl, allyl, cyclopentyl, cyclohexyl, phenyl, and benzyl.

3. The lithium regent-porous oxide composition of claim 2, wherein the lithium metal is loaded up to about 40% by weight, the pores of the porous oxide have an average pore size of 10 Å to 500 Å, and the porous oxide is selected from porous alumina, porous titanium oxide, porous calcium oxide, porous zirconia, porous iron oxide, porous Co$_3$O$_4$, porous metal phosphate, porous hybrid phosphosilicate, porous aluminates, porous vanadates, and molybadates.

4. The lithium reagent-porous oxide composition of claim 3, wherein the porous oxide is alumina.

5. The lithium reagent-porous oxide composition of claim 1, wherein R is R$^1$R$^2$N, R$^1$ is selected from the group consisting of methyl, ethyl, n-propyl, isopropyl, n-butyl, t-butyl, isobutyl, sec-butyl, ethenyl, allyl, cyclopentyl, cyclohexyl, phenyl, and benzyl; and R$^2$ is selected from the group consisting of hydrogen, methyl, ethyl, n-propyl, isopropyl, n-butyl, t-butyl, isobutyl, sec-butyl, ethenyl, allyl, cyclopentyl, cyclohexyl, phenyl, and benzyl.

6. The lithium reagent-porous oxide composition of claim 5, wherein the lithium metal is loaded up to about 40% by weight, the pores of the porous oxide have an average pore size of 30 Å to 500 Å, and the porous oxide is selected from porous alumina, porous titanium oxide, porous calcium oxide, porous zirconia, porous iron oxide, porous $CO_2O_4$, porous metal phosphate, porous hybrid phosphosilicate, porous aluminates, porous vanadates, and molybdates.

7. The lithium reagent-porous oxide composition of claim 6, wherein the porous oxide is alumina.

8. The lithium reagent-porous oxide composition of claim 1, wherein the RLi is loaded up to about 40% by weight, the pores of the porous oxide have an average pore size of 30 Å to 500 Å, and the porous oxide is selected from porous alumina, porous titanium oxide, porous calcium oxide, porous zirconia, porous iron oxide, porous $Co_3O_4$, porous metal phosphate, porous hybrid phosphosilicate, porous aluminates, porous vanadates, and molybdates.

9. The lithium reagent-porous oxide composition of claim 8, wherein the porous oxide is alumina.

10. The lithium reagent-porous oxide composition of claim 1, wherein the lithium metal is loaded to about 20% to 40% by weight.

11. The lithium reagent-porous oxide composition of claim 1, wherein the porous oxide is alumina.

12. The lithium reagent-porous oxide composition of claim 1, wherein the pores of the porous oxide have an average pore size of 6.0 Å to 190 Å.

13. A chemical reaction comprising the step of reacting an organolithium reagent or a lithium amide reagent with another reactant, the improvement wherein the organolithium reagent or the lithium amide reagent is the lithium reagent-porous oxide composition of claim 1.

14. The chemical reaction of claim 13, wherein the chemical reaction is selected from the group consisting of nucleophilic addition reactions, polymerization reactions, and base-catalyzed reactions.

15. The chemical reaction of claim 13, wherein the chemical reaction is selected from the group consisting of:
  a nucleophilic addition to a carbon centered electrophile;
  preparation of organocuprate or Gilman's reagent;
  preparation of organophosphorous, organosulfur, organoboron, organotin compounds from appropriate electrophiles;
  preparation of lithium amides;
  a directed ortho-lithiation and subsequent quenching with electrophiles;
  preparation of enolates or other deprotonations;
  an initiator for anionic polymerizations;
  generation of Ylides in Wittig reaction;
  generation of carbine;
  isotopic labeling;
  a Shapiro reaction;
  a non-nucleophilic base reaction;
  preparation of organolithium compounds by halogen-metal exchange or reductive cleavage of C—O, C—S or C—P bonds;
  reduction of cabonyls or aromatics (Birch reduction); and
  generation of reactive intermediates.

16. The chemical reaction of claim 13, wherein the chemical reaction occurs in a conventional batch reaction or in a process flow reactor.

* * * * *